United States Patent [19]

Uhlen et al.

[11] Patent Number: 5,534,424
[45] Date of Patent: Jul. 9, 1996

[54] CHEMICAL METHOD FOR THE ANALYSIS OF DNA SEQUENCES

[75] Inventors: Mathias Uhlen, Upsala; Joakim Lundeberg, Stockholm, both of Sweden

[73] Assignee: Cemu Bioteknik AB, Upsala, Sweden

[21] Appl. No.: 331,552

[22] PCT Filed: May 12, 1993

[86] PCT No.: PCT/EP93/01203

§ 371 Date: Apr. 18, 1995

§ 102(e) Date: Apr. 18, 1995

[87] PCT Pub. No.: WO93/23562

PCT Pub. Date: Nov. 25, 1993

[30] Foreign Application Priority Data

May 12, 1992 [GB] United Kingdom .................. 9210176

[51] Int. Cl.$^6$ ............................. C12P 19/34; C12Q 1/70; C12Q 1/68; C07H 21/04
[52] U.S. Cl. .................. 435/91.2; 435/5; 435/6; 536/24.3; 536/24.33
[58] Field of Search .................. 435/6, 5, 91.5, 435/91.2; 536/24.3, 24.33

[56] References Cited

U.S. PATENT DOCUMENTS

| | | | |
|---|---|---|---|
| 4,654,267 | 3/1987 | Ugelstad et al. | 428/407 |
| 5,135,717 | 8/1992 | Renzoni et al. | 422/61 |
| 5,405,746 | 4/1995 | Uhlen et al. | 435/6 |

FOREIGN PATENT DOCUMENTS

| | | |
|---|---|---|
| 0412883 | 2/1991 | European Pat. Off. |
| 0469755 | 2/1992 | European Pat. Off. |
| 0530112 | 3/1992 | European Pat. Off. |
| WO89/09282 | 10/1989 | WIPO |
| 89/09283 | 10/1989 | WIPO |
| 89/12063 | 12/1989 | WIPO |
| WO90/11369 | 10/1990 | WIPO |
| 93/08305 | 4/1993 | WIPO |
| WO93/23564 | 11/1993 | WIPO |
| WO93/23563 | 11/1993 | WIPO |

OTHER PUBLICATIONS

Jalanko et al. "Screening for defined Cystic Fibrosis Mutations by Solid phase Minisequencing", Clin. Chem, 38(1) 39–43. 1992.
Lea et al., "Monosized, Magnetic Polymer Particles: Their Use in Separation of Cells and Subcellular Components and in the Study of Lymphocyte Function in vitro", J. Mol. Recogn., vol. 1, No. 1, 1988, pp. 10–18.
Hultman et al., "Bidirectional Solid–Phase Sequencing of in Vitro–Amplified Plasmid DNA", Biotechniques, vol. 10, No. 1, (1991), pp. 84–93.
Langley et al., "Molecular Basis of β–Galactosidase α–Complementation", Proc. Nat. Acad. Sci. USA, vol. 72, No. 4, (1975) pp. 1254–1257.
Hultman et al., "Approaches to Solid Phase DNA Sequencing", Nucleosides & Nucleotides, 7(5&6), 1988 pp. 629–638.
Ruether et al., "pUR 250 Allows Rapid Chemical Sequencing of both DNA Strands of its Inserts", Nucleic Acids Research, vol. 10, No. 19 (1982), pp. 5764–5773.
Fahy et al., "Self–Sustained Sequence Replication (3SR): An Isothermal Transcription–based Amplification System Alternative to PCR", PCR Methods and Applications, 1991, pp. 25–33.
Almer, "Surface Modification of Polymers", Doctoral Thesis, Royal Institute of Technology, 1988. pp.1–35.
Hultman et al., "Direct Solid Phase Sequencing of Genomic and Plasmid DNA Using Magnetic Beads as Solid Support", Nucleic Acids Research, vol. 17, No. 13 (1988), pp. 4937–4946.
Wahlberg et al., "General Colorimetric Method for DNA Diagnostics Allowing Direct Solid–Phase Genomic Sequencing of the Positive Samples", Proc. Natl. Acad. USA, vol. 87 (1990), pp. 6569–6573.
Barany, "The Ligase Chain Reaction in a PCR World", PCR Methods and Applications, 1991, pp. 5–16.
Nyren et al., "Solid Phase DNA Minisequencing By an Enzymatic Luminometric Inorganic Pyrophosphate Detection Assay", Analytical Biochemistry, vol. 208:171–175, (1993).

Primary Examiner—W. Gary Jones
Assistant Examiner—Dianne Rees
Attorney, Agent, or Firm—Foley & Lardner

[57] ABSTRACT

The invention provides a method of identification of the base in a target position in a DNA sequence wherein sample DNA is subjected to amplification; the amplified DNA is immobilised and then subjected to strand separation, the non-immobilised strand being removed and an extension primer, which hybridises to the immobilised DNA immediately adjacent to the target position, is provided; each of four aliquots of the immobilised single stranded DNA is then subjected to a polymerase reaction in the presence of a dideoxynucleotide, each aliquot using a different dideoxynucleotide whereby only the dideoxynucleotide whereby only the dideoxynucleotide complementary to the base in the target position becomes incorpored; the four aliquots are then subjected to extension in the presence of all four deoxynucleotides, whereby in each aliquot the DNA which has not reacted with the dideoxynucleotide is extended to form double stranded DNA while the dideoxy-blocked DNA remains as non-extended DNA; followed by identification of the double stranded and/or non-extended DNA to indicate which dideoxynucleotide was incorporated and hence which base was present in the target position.

7 Claims, 4 Drawing Sheets

5'-CGTTGTAAAACGACGGCCAGT

RIT135

ATCCATACAATACTCCAGTATTTGC-3'

5'— AAAATCCATACAATACTCCAGTATTTGCCATAAAGAAAAAAGACAGTACTAAATGG 625　　　　　　　　　　　　　　　　　　　　　　　　674

RIT332

5'-CATCTGTTGAAGTGGGGACTT-3'

AGACATCTGTTGAAGTGGGGACTTACC

1107

1165

CTTTGGATGGGTTATGAACTCCATCCTG — 3'

3'-GAAACCTACCCAATACTTGGGGTTAACAATAGGCGAGTGTTAACATCGATG-Biotin-5'

GGTTAACAATAGGCGAG-5'

RIT321　　　　　　　　　RIT322 lac op

FIG. 3

RIT333

5'-CCCGGGATCCATACACAATACTCCAGTATTGC-3'

5'—AAAATCCATACACAATACTCCAGTATTTGCCATAAAGAAAAAGACAGTACTAAATGG
              |
             625

RIT331

3'-GAAACCTACCAATACTTGAGGTAG
                           CTTAAGCC-5'
                             |
                            1165

CTTGGATGGTTATGAACTCCATCCTG—3'

AGACATCTGTTGAAGTGGGGACTTACC

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 56 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:1:

```
AAAATCCATA  CAATACTCCA  GTATTTGCCA  TAAAGAAAAA  AGACAGTACT  AAATGG        5 6
```

( 2 ) INFORMATION FOR SEQ ID NO:2:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:2:

```
AGACATCTGT TGAAGTGGGG ACTTACC                                    27
```

( 2 ) INFORMATION FOR SEQ ID NO:3:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:3:

```
CTTTGGATGG GTTATGAACT CCATCCTG                                   28
```

( 2 ) INFORMATION FOR SEQ ID NO:4:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:4:

```
CGTTGTAAAA CGACGGCCAG TATCCATACA ATACTCCAGT ATTTGC               46
```

( 2 ) INFORMATION FOR SEQ ID NO:5:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:5:

```
CATCTGTTGA AGTGGGGACT T                                          21
```

( 2 ) INFORMATION FOR SEQ ID NO:6:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:6:

```
GAAACCTACC CAATACTTGG GTTAACAATA GGCGAG                          36
```

( 2 ) INFORMATION FOR SEQ ID NO:7:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:7:

```
GGGTTAACAA TAGGCGAGTG TTAACATCGA TG                              32
```

( 2 ) INFORMATION FOR SEQ ID NO:8:

( i ) SEQUENCE CHARACTERISTICS:
  ( A ) LENGTH: 31 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:8:

CCCGGGATCC ATACAATACT CCAGTATTTG C  31

( 2 ) INFORMATION FOR SEQ ID NO:9:

( i ) SEQUENCE CHARACTERISTICS:
  ( A ) LENGTH: 34 base pairs
  ( B ) TYPE: nucleic acid
  ( C ) STRANDEDNESS: single
  ( D ) TOPOLOGY: linear  ( x i ) SEQUENCE DESCRIPTION: SEQ ID NO:9:

GAAACCTACC CAATACTTGA GGTAGCTTAA GCCC  34

CHEMICAL METHOD FOR THE ANALYSIS OF DNA SEQUENCES

This invention relates to a novel method for identifying a base in a target position in a DNA sequence.

In the diagnostic or forensic use of DNA analysis, full sequencing of target DNA may be unnecessary where the detection of a single base variation or mismatch is sufficient to provide the required information. Such a single base variation or mismatch may for example arise from a point mutation or, in fact, any deletion or insertion of genetic material where the detection of the first irregular base in the sequence will give the required diagnostic information. Thus, Allelic Specific PCR has been developed whereby PCR (polymerase chain reaction) is carried out on a sample using a pair of primers for the target DNA one of which is relatively short and will hybridise to one allelic locus of the DNA but not to the other allelic sequence. Failure to amplify is thus indicative that the non-hybridising allele of the DNA was present but unfortunately the conditions required to obtain reliable hybridisation to the normal DNA are difficult to achieve in practice.

It has been proposed to carry out PCR using probes hybridising to positions away from the target mutation or area of allelic variation, followed by use of a labelled probe which will not hybridise to the mutated region or area of allelic variation. However, this also commonly gives false negatives.

A method of detecting allele-specific DNA called the Ligase Chain Reaction (LCR) has recently been developed and has been reviewed by F. Barang (PCR Methods and Applications Vol.1, 5–16). Two different oligonucleotides, which hybridise adjacent to each other on complementary DNA, are required and the products of LCR need to be separated on a polyacrylamide gel before a result can be determined.

Full length sequencing, particularly solid phase sequencing, as described in WO 89/09282 gives accurate results but is more demanding and may thus not be appropriate for diagnostic screening in some instances.

The present invention is based on the concept of using a polymerase reaction on four aliquots of amplified and immobilised DNA of interest in single stranded form. Each aliquot uses the same specific extension primer and a different dideoxynucleotide but no deoxynucleotides so that only the dideoxynucleotide complementary to the base in the target position is incorporated; the target position being directly adjacent to the 3' end of the specific extension primer hybridising to the DNA. Put another way, the target position on the immobilised strand is immediately 5' of where the specific primer hybridises to the DNA. Chain extension using normal deoxynucleotides is then effected (a so-called chase reaction) using the specific primer so that the dideoxy-blocked DNA will remain unreacted while the un-blocked DNA will form double stranded DNA. Various methods may then be used to distinguish double stranded DNA from non-extended DNA, i.e. substantially single stranded DNA, and thus enable the base in the target position to be identified.

The invention thus provides a method of identification of the base in a target position in a DNA sequence wherein sample DNA is subjected to amplification; the amplified DNA is immobilised and then subjected to strand separation, the non-immobilised strand being removed and an extension primer, which hybridises to the immobilised DNA immediately adjacent to the target position, is provided; each of four aliquots of the immobilised single stranded DNA is then subjected to a polymerase reaction in the presence of a dideoxynucleotide, each aliquot using a different dideoxynucleotide whereby only the dideoxynucleotide complementary to the base in the target position becomes incorporated; the four aliquots are then subjected to extension in the presence of all four deoxynucleotides, whereby in each aliquot the DNA which has not reacted with the dideoxynucleotide is extended to form double stranded DNA while the dideoxy-blocked DNA remains as non-extended DNA; followed by identification of the double stranded and/or non-extended DNA to indicate which dideoxynucleotide was incorporated and hence which base was present in the target position.

The term dideoxynucleotide as used herein includes all 2'-deoxynucleotides in which the 3'-hydroxyl group is absent or modified and thus, while able to be added to the primer in the presence of the polymerase, is unable to enter into a subsequent polymerisation reaction.

Preferably, the sample DNA is amplified in vitro by PCR although amplification by other methods may be used such as in vitro Self Sustained Sequence Replication (3SR) or in vivo in a vector, and, if desired, in vitro and in vivo amplification may be used in combination. Whichever method of amplification is used it is desirable that the amplified DNA becomes immobilised or is provided with means for attachment to a solid support. For example, a PCR primer may be immobilised or be provided with means for attachment to a solid support. Also, a vector may comprise means for attachment to a solid support adjacent the site of insertion of the sample DNA such that the amplified sample DNA and the means for attachment may be excised together.

In the PCR method a pair of polymerisation primers specific to known sequences of the target DNA are selected, one hybridising at or near the 5' end of one of the strands and the other at or near the 5' end of the complementary strand such that in the presence of a polymerase, each primer produces a DNA sequence extending the full length of the target DNA template. If the DNA so produced is then subjected to strand separation, typically by melting at a temperature of about 90° C., the newly formed single stranded DNA sequences will hybridise to excess primer present in the mixture, usually after reducing the temperature to the range suitable for annealing, whereupon in the presence of the polymerase, further DNA strands are synthesised, this time extending only between the termini of the two primers. The polymerase is preferably capable of surviving the high temperature used in the strand separation step, a suitable thermophilic polymerase, namely Taq, having recently become available. If an excess of the two primers and of nucleotides needed for DNA synthesis is maintained in the medium, it is possible to operate a repeated cyclic process in which the separate strands are synthesised, separated, annealed to primer and new strands synthesised, merely by raising and lowering the temperature between the optimal temperatures for each of the above stages. In this way, it is found that amplification of the original target DNA can be exponential and million-fold increases of concentration can be effected in a relatively short time.

It is desirable that when PCR is used its effectiveness is assessed, e.g. to determine whether or not sufficient DNA has been formed to give clear results with a relatively low level of background. Various tests are known in the art but we prefer to use the solid phase approach we described earlier for detection of immobilised amplified nucleic acids, designated DIANA (PCT/EP90/00454 [WO90/11369]), which has been used for example in its preferred embodiment in the colorimetric detection of in vitro amplified DNA. The assay is based on the use of a biotinylated or otherwise functionalised PCR primer, which is used to capture in vitro amplified material on, for example, streptavidin-coated magnetic beads. The other PCR primer contains a "handle", such as a lac operator sequence, allowing colorimetric detection of the captured DNA using a LacI repressor-β-galactosidase fusion protein. (Wahlberg, J., Lundeberg, J., Hultman, T. and Uhlén, M. (1990) "General colorimetric method for DNA diagnostics allowing direct solid-phase genomic sequencing of the positive samples." Proc. Natl. Acad. Sci U.S.A. 87, 6569–6573). The preferred form of the qualitative DIANA assay combines the advantages of the PCR method with the high specificity and stability of the biotin-streptavidin system and the simplicity of a colorimetric detection based on β-galactosidase. The strong interaction between biotin and streptavidin ($K_d=10^{-15}$ $M^{-1}$) accentuates the efficiency of the system. The magnetic beads as solid support ensure that no centrifugations, filtrations or precipitations are needed (T. Hultman, S. Ståhl, E. Hornes and M. Uhlén Nucl. Acids Res. 17, 4937 (1989)). However, it is preferred in the method according to the present invention to use the same PCR primer both as the means of immobilisation and for the incorporation of the lac operator sequence.

A number of proteins are known which bind to specific DNA sequences and are often involved in genetic processes such as switching operons on and off. One such protein is the lac repressor LacI which reacts with the lac operator (lacOP) to inhibit transcription. Thus, if the recognition site is the DNA sequence lacOP, the label can be attached via the protein LacI. It is particularly convenient to devise a fusion protein of a DNA binding protein such as LacI with a further protein which can be subsequently used for detection for example using methods based on colour fluorescence or chemiluminescence. Examples of such proteins are β-galactosidase, alkaline phosphatase and peroxidase.

It is preferred to use as a label a LacI repressor-β-galactosidase fusion protein which recognises a 21 base pair lac operator sequence introduced at the end of the amplified DNA. The lac operator sequence may be introduced for example by one of the PCR primers if used, preferably the immobilised primer, or the sequence may be in an amplification vector in a suitable position for excision with the amplified sample DNA. The fusion protein will bind to the lac OP sequence of the DNA and the addition of ONPG (ortho-nitrophenyl-β-D-galactoside) will lead to a colour formation which can be assessed spectrophotometrically. Use of this fusion protein and ONPG (ortho-nitrophenyl-β-D-galactoside) allows for a fast simple colorimetric assay which does not have the safety problems associated with using radiolabels. IPTG (n-isopropyl-β-D-thiogalactopyranoside) for example, can be added to release the fusion protein from the DNA.

Two-stage PCR (using nested primers), as described in our co-pending application PCT/EP90/00454 (WO90/11369), may be used to enhance the signal to noise ratio and thereby increase the sensitivity of the method according to the invention. By such preliminary amplification, the concentration of target DNA is greatly increased with respect to other DNA which may be present in the sample and a second-stage amplification with at least one primer specific to a different sequence of the target DNA significantly enhances the signal due to the target DNA relative to the 'background noise'.

Any suitable polymerase may be used, although it is preferred to use a thermophilic enzyme such as Taq polymerase to permit the repeated temperature cycling without having to add further polymerase, e.g. Klenow fragment, in each cycle of PCR.

Regardless of whether one-stage or two stage PCR is performed, the efficiency of the PCR is not critical since the invention relies on the distinct difference between the aliquots. However, as mentioned above, it is preferred to run an initial qualitative DIANA as a check for the presence or absence of amplified DNA.

Immobilisation of the amplified DNA may take place as part of PCR amplification itself, as where one or more primers are attached to a support, or alternatively one or more of the PCR primers may carry a functional group permitting subsequent immobilisation, e.g. a biotin or thiol group. Immobilisation by the 5' end of a primer allows the strand of DNA emanating from that primer to be attached to a solid support and have its 3' end remote from the support and available for subsequent hybridisation with the extension primer and chain extension by polymerase.

The present invention includes a particularly useful primer which comprises, reading 5' to 3', means permitting immobilisation of said primer, a sequence which is bound by a DNA binding protein, and a sequence capable of hybridising at or near the 5' end of a strand of target DNA. Use of such a primer allows for immobilisation and the ability to determine whether or not double stranded DNA is formed in a polymerisation step substantially up to the point of immobilisation. It will be clear that several nucleotides may intervene between the means permitting immobilisation and the sequence which is bound by a DNA binding protein or between that sequence and the sequence capable of hybridising to target DNA.

Preferably, the means permitting immobilisation is biotin although other functional groups, such as thiol groups, may be used. However, biotin is preferred because of its strong interaction with streptavidin and the relative ease by which it can be incorporated into a primer. The sequence which is bound by a DNA binding protein is preferably the lac operator which is reversibly bound by the lac I repressor protein.

The solid support may conveniently take the form of microtitre wells, which are advantageously in the conventional 8×12 format, or dipsticks which may be made of polystyrene activated to bind the primer DNA (K Almer, Doctoral Theses, Royal Institute of Technology, Stockholm, Sweden, 1988). The support may also comprise particles, fibres or capillaries made, for example, of agarose, cellulose, alginate, Teflon® or polystyrene. The support may also comprise magnetic particles e.g. the superparamagnetic beads produced by Dynal AS (Oslo, Norway).

The solid support may carry functional groups such as hydroxyl, carboxyl, aldehyde or amino groups, or other moieties such as avidin or streptavidin, for the attachment of primers. These may in general be provided by treating the support to provide a surface coating of a polymer carrying one of such functional groups, e.g. polyurethane together with a polyglycol to provide hydroxyl groups, or a cellulose derivative to provide hydroxyl groups, a polymer or copolymer of acrylic acid or methacrylic acid to provide carboxyl groups or an aminoalkylated polymer to provide amino groups. U.S. Pat. No. 4,654,267 describes the introduction of many such surface coatings.

The assay technique is very simple and rapid, thus making it easy to automate by using a robot apparatus where a large number of samples may be rapidly analysed. Since the preferred detection and quantification is based on a colorimetric reaction a visual analysis is often sufficient for evaluation.

The target DNA may be cDNA synthesised from RNA in the sample and the method of the invention is thus applicable to diagnosis on the basis of characteristic RNA. Such preliminary synthesis can be carried out by a preliminary treatment with a reverse transcriptase, conveniently in the same system of buffers and bases of subsequent PCR steps if used. Since the PCR procedure requires heating to effect strand separation, the reverse transcriptase will be inactivated in the first PCR cycle. When mRNA is the sample nucleic acid, it may be advantageous to submit the initial sample, e.g. a serum sample, to treatment with an immobilised polydT oligonucleotide in order to retrieve all mRNA via the terminal polyA sequences thereof. Alternatively, a specific oligonucleotide sequence may be used to retrieve the RNA via a specific RNA sequence. The oligonucleotide can then serve as a primer for cDNA synthesis, as described in International Patent Application PCT/89EP/00304 (WO89/09282).

PCR has been discussed above as a preferred method of initially amplifying target DNA although the skilled person will appreciate that other methods may be used instead of in combination with PCR. A recent development in amplification techniques which does not require temperature cycling or use of a thermostable polymerase is Self Sustained Sequence Replication (3SR). 3SR is modelled on retroviral replication and may be used for amplification (see for example Gingeras, T. R. et al PNAS (USA) 87:1874–1878 and Gingeras, T. R. et al PCR Methods and Applications Vol. 1, pp 25–33).

Advantageously, the extension primer is sufficiently large to provide appropriate hybridisation with the immobilised strand immediately adjacent the target position, yet still reasonably short in order to avoid unnecessary chemical synthesis. It will be clear to persons skilled in the art that the size of the extension primer and the stability of hybridisation will be dependent to some degree on the ratio of A-T to C-G base pairings, since more hydrogen bonding is available in a C-G pairing. Also, the skilled person will consider the degree of homology between the extension primer to other parts of the amplified sequence and choose the degree of stringency accordingly. Guidance for such routine experimentation can be found in the literature, for example, Molecular Cloning: a laboratory manual by Sambrook, J., Fritsch, E. F. and Maniatis, T. (1989). The extension primer is preferably added before the sample is divided into four aliquots although it may be added separately to each aliquot. It should be noted that the extension primer may be identical with the PCR primer but preferably it is different, to introduce a further element of specificity into the system.

The polymerase reaction in the presence of dideoxy nucleotides is carried out using a polymerase which will incorporate dideoxynucleotides, e.g. T7 polymerase, Klenow or Sequenase® Ver. 2.0 (USB U.S.A.). However, it is known that many polymerases have a proof-reading or error checking ability and that 3' ends available for chain extension are sometimes digested by one or more nucleotides. If such digestion occurs in the method according to the invention the level of background noise increases. In order to avoid this problem it is preferable to use a non proof-reading polymerase, e.g. T7 polymerase or Sequenase. Otherwise it is desirable to add to each aliquot fluoride ions or nucleotide monophosphates which suppress 3' digestion by polymerase.

Identification of the double stranded and/or non-extended DNA is possible via a variety of means. With regard to the double stranded DNA, conventional techniques such as radiolabel incorporation during chain extension are possible but it is preferred to use the lac operator sequence which is preferably incorporated into the DNA during amplification, as discussed above. Full chain extension creates the double stranded DNA sequence which is bound by the lac I repressor-βgalactosidase fusion protein. Bound fusion protein can then be identified colorimetrically as discussed above and this identifies the three aliquots which have been extended, thereby identifying the dideoxy base which was added in the remaining aliquot.

With regard to the non-extended DNA, where extension of the primer was blocked by a dideoxynucleotide, again a number of means for identification are possible and will be readily apparent to the skilled person. Preferably, a probe which hybridises downstream of the 3' end of the extension primer is used, i.e. the probe hybridises to the immobilised strand between the site of hybridisation of the extension primer and the 5' end of the immobilised strand. The probe is suitably labelled or provided with means for attaching a label. Such a probe will bind to the single strand DNA but will not bind to the double stranded DNA.

If desired, both double and single stranded DNA can be identified and this provides additional checking for the accuracy of the results. It will usually be desirable to run a control with no dideoxynucleotides and a 'zero control' containing a mixture of all four dideoxynucleotides.

Another means of identification is that disclosed in our co-pending application of even date (PCT/EP93/01205 [WO93/23564]) which relates to detection of pyrophosphate released during chain extension. When each nucleotide is incorporated, a pyrophosphate group is split off the nucleotide triphosphate and the remaining nucleotide monophosphate is incorporated at the end of the growing nucleic acid chain. In those aliquots which have not incorporated a chain terminating dideoxynucleotide there is extensive pyrophosphate release during chain extension. This release of pyrophosphate can be measured using luciferin and luciferase which emit light in substantially direct proportion to the amount of pyrophosphate present.

In many diagnostic applications, for example genetic testing for carriers of inherited disease, the sample will contain heterozygous material, that is half the DNA will have one nucleotide at the target position and the other half will have another nucleotide. Thus of the four aliquots used in the method of the invention, two will show a positive signal and two will show half the positive signal. It will be seen therefore that it is desirable to quantitatively determine the amount of label detected in each sample. In the case of a homozygous sample it will be clear that there will be three negative and one positive signal of the four aliquots.

Advantageously, the method according to the present invention may be combined with the method taught in our co-pending patent application of even date (PCT/EP93/01204 [WO93/23563]) which uses PCR to introduce loop structures which provide a permanently attached 3' primer at the 3' terminal of a DNA strand of interest. For example, in such a modified method, the extension primer is introduced as part of the 3'-terminal loop structure onto a target sequence of one strand of double stranded DNA which contains the target position, said target sequence having a region A at the 3'-terminus thereof and there being optionally a DNA region B which extends 3' from region A, whereby said double-stranded DNA is subjected to polymerase chain reaction (PCR) amplification using a first primer hybridising to the 3'-terminus of the sequence complementary to the target sequence, which first primer is immobilised or provided with means for attachment to a solid support, and a second primer having a 3'-terminal sequence which hybridises to at least a portion of A and/or B of the target sequence while having at its 5'-end a sequence substantially identical to A, said amplification producing double-stranded target DNA having at the 3'-end of the target sequence, in the following order, the region A, a region capable of forming a loop and a sequence A' complementary to sequence A, whereafter the amplified double-stranded DNA is subjected in immobilised form to strand separation whereby the non-immobilised target strand is liberated and region A' is permitted or caused to hybridise to region A, thereby forming said loop. The 3' end of region A' hybridises immediately adjacent the target position. The dideoxy and extension reactions use the hybridised portion as a primer and the base incorporated at the target position can be identified in any manner, preferably by pyrophosphate release as taught by our co-pending PCT/EP93/01205 (WO93/23564) application mentioned above.

The invention also comprises kits which will normally include at least the following components:

(a) a test specific extension primer which hybridises to sample DNA so that the target position is directly adjacent to the 3' end of the primer;

(b) a polymerase;

(c) deoxynucleotides and dideoxynucleotides; and (d) optionally a solid support.

If the kit is for use with initial PCR amplification then it will also normally include at least the following components:

(i) a pair of primers for PCR at least one primer having means permitting immobilisation of said primer;

(ii) a polymerase which is preferably heat stable, for example Taq1 polymerase;

(iii) buffers for the PCR reaction; and (iv) deoxynucleotides.

Where an enzyme label is used, the kit will advantageously contain a substrate for the enzyme and other components of a detection system.

Preferably, one of the primers will include both means permitting immobilisation of said primer and a sequence which is bound by protein. A preferred form of primer comprises biotin to act as the means permitting immobilisation, eg to an avidin or streptavidin coated surface, and the lac operator as the means permitting labelling. The kit for carrying out the invention using a preferred primer of the type described above would preferably contain an enzyme label conjugated to the lac I repressor protein; a preferred enzyme label being β-galactosidase.

The invention will now be described by way of non-limiting examples with reference to the drawings in which.

MATERIALS AND METHODS

Bacterial strains and plasmids. *Escherichia coli* RRIΔM15 (Rüther, U.(1982). pUR 250 which allows rapid chemical sequencing of both strands of its inserts (Nucl. Acids Res., 10, 5765–5722) was used as bacterial host. The plasmid vector used was pRIT 28 (Hultman, T., Ståhl, S., Moks, T. and Uhlén, M. (1988) "Approaches to Solid Phase DNA Sequencing", Nucleosides & Nucleotides. 7, 629–638).

Figure 2:
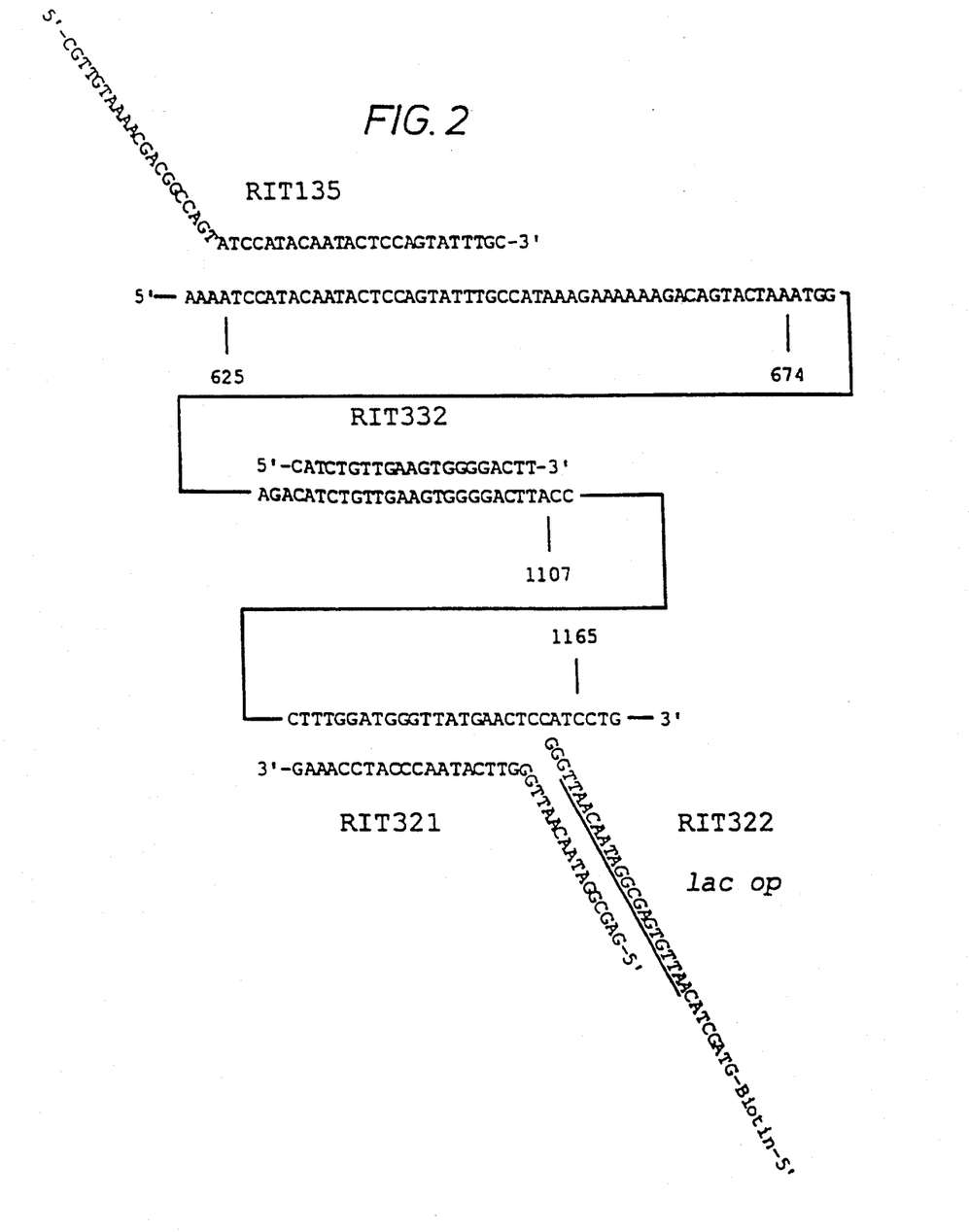
FIG. 2 shows oligonucleotide primers (SEQ ID Nos. 4–7) used in Example 1 together with sample DNA for amplification (SEQ ID Nos. 1–3)
Figure 3:
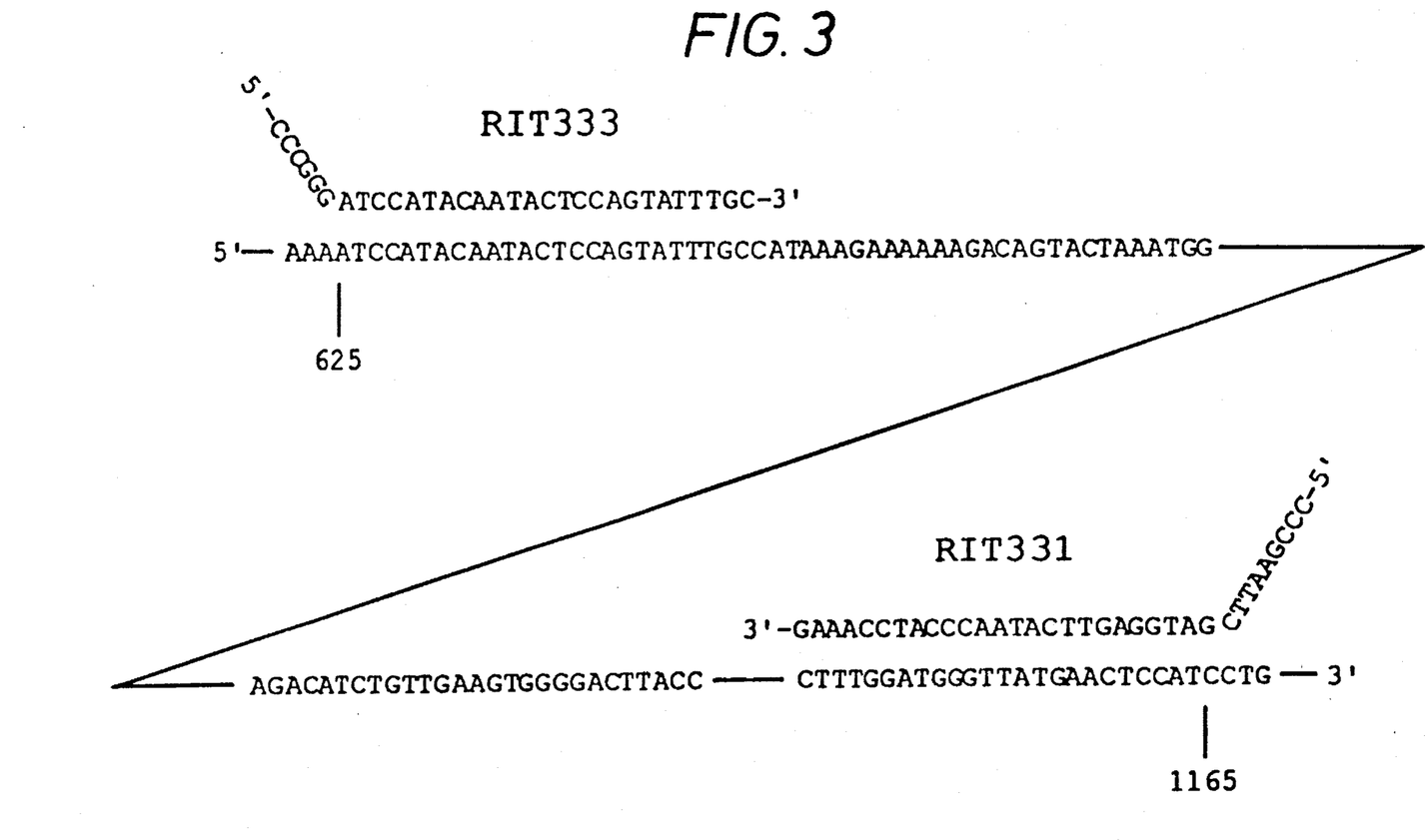
FIG. 3 shows further oligonucleotide primers (SEQ ID Nos. 8 and 9) used in the Example together with the sample DNA (SEQ ID Nos. 1–3)

Synthesis of oligonucleotides. 7 oligonucleotide primers (See FIGS. 2 and 3), RIT 135 (SEQ ID No:4), RIT 321 (SEQ ID No:6), RIT 322 (SEQ ID No:7), RIT 331 (SEQ ID No:9), RIT 332 (SEQ ID No:5) and RIT 333 (SEQ ID No:8), complementary to regions (SEQ ID Nos 1–3) encoding a part of the active site of the HIV reverse transcriptase gene (RT) (bases 625 to 1165 Myers, G., Korber, B., Berkovsky, J. A. Smith, R. F. and Pavlakis, G. N. Human Retroviruses and AIDS 1991 (Los Alamos National Laboratory, New Mexico 1991)), were synthesized by phosphoramidite chemistry on an automated DNA synthesis apparatus (Gene Assembler Plus®, KABI-Pharmacia, Sweden) as described by the manufacturer. RIT322 was biotinylated by using a biotin phophoramidite (Clonetech, Calif., U.S.A.). Purification was performed on a pepRPC 5/5 reversed phase column (KABI-Pharmacia, Sweden).

Enzymes and nucleotides. Restriction enzymes, T4 DNA ligase (KABI-Pharmacia, Sweden), T7 DNA polymerase (KABI-Pharmacia, Sweden), Taq DNA polymerase (Cetus, Calif. U.S.A.) and Sequenase® ver 2.0 (USB U.S.A.) were used in accordance with the supplier's recommendations. Deoxy and dideoxynucleotides were obtained from Boehringer Mannheim, Germany.

PCR cloning

The HIV RT fragment was cloned by amplification from a clinical sample obtained from a patient with HIV-1 (Swedish Bacteriology Laboratory, SBL, Stockholm, Sweden) using 5 pmol each of the oligonucleotides RIT331 and RIT333 (FIG. 3) both containing "handles" in order to introduce an upstream Bam HI and a downstream Eco RI recognition sites. The PCR reaction mix contained 200 μM dNTPs, 20™(polyoxyethylene sorbitan monolamate) mM Tris-HCl (pH 8.7), 2 mM $MgCl_2$, 0.1% Tween® 20 and 0.5 units AmpliTaq™ resulting in a final volume of 50 μl . The temperature profile was set up by a denaturation step at 95° C. for 0.5 min. followed by a primer annealing step at 55° C. for 0.5 min. and a final extension step at 72° C. for 2 mins. These steps were repeated 30 times using a Gene Amp PCR System, PE 9600 (Perkin Elmer, Calif., U.S.A.). The PCR amplified HIV RT fragment and the pRIT 28 vector were both restricted with Bam H1 and Eco R1, cut out and purified from agarose and then ligated for 1 hour in room temperature. The construction was transformed into competent RRIΔM15cells and spread on TBAB (Sambrook, J., Fritsch, E. F. and Maniatis, T. (1989) loc.cit. plates containing IPTG(n-isopropyl-β-D-thiogalactopyranoside), X-gal (5-bromo-4-chloro-3-indolyl-β-D-galactoside) and ampicillin allowing blue/white selection (Langley, E. K. Villarejo, M. R. Fowler, A. V. Zamenhof, P. J. and Zabin, I. (1975). Proc. Natl. Acad. Sci. U.S.A. 72, 1254–1257). Five white colonies containing the plasmid with a correct insert was confirmed by solid phase sequencing (Hultman, T., Bergh, S., Moks, T and Uhlén, M. (1991) "Bidirectional solid-phase sequencing of in vitro-amplified plasmid DNA". Bio Techniques 10, 84–93.). One of those clones was designated pRIT-RT and choosen for further studies. This clone is stored at the Department of Biochemistry, Royal Institute of Technology, Stockholm, Sweden.

Template preparation for DIANA detected Mini Sequencing

A colony harbouring pRIT28-RT was transferred to a vial and lysed at 99° C. for 5 min. in 10 μl 20 mM Tris-HCl (pH 8.7). 1 μl lysate was subsequently transferred to a PCR mixture of 5 pmol RIT135 and RIT322 (biotinylated), 0.25 pmol RIT321, 200 μM dNTPs, 20 mM Tris-HCl (pH 8.7), 2 mM MgCl$_2$, 0.1% Tween 20™ and 0.5 units AmpliTaq™ to a final volume of 50 µl. It will be noted that primer RIT322 comprises a 5' Biotin, for subsequent attachment to a streptavidin coated solid support, and the 21 bases which define the lac Op recognition sequence. Amplification was performed as above and the resulting PCR product was subsequently immobilized (Hultman, T. Ståhl, S., Hornes, E. and Uhlén, M. (1989) "Direct solid phase sequencing of genomic and plasmid DNA using magnetic beads as solid support". Nucl. acids Res. 17, 4937–4946) on prewashed streptavidin coated paramagnetic beads, (Lea, T., Vartdal, F., Nustad, K., et al. (1988). "Monosized, magnetic polymer particles: and their use in separation of cells and subcellular components and in the study of lymphocyte function in vitro". Journal of Molecular Recognition 1, 9–18) Dynabeads® M280-Streptavidin (Dynal AS, Norway), prewashed with binding solution according to manufacturer. After immobilization, the beads were rinsed with 50 µl binding-washing solution and assayed for bound DNA. The beads with the immobilized DNA were mixed with 50 µl of the fusion protein, lacI-β-galactosidase (Dynal AS, Norway), and incubated for 20 minutes. Excess of the fusion protein was removed by washing the beads 4 times with DIANA buffer (Dynal AS, Norway) and changing to new tubes in the last step in order to avoid background due to coating of the walls. 100 µl of chromogenic substrate, ortho-nitrophenyl-β-D-galactoside (ONPG, 1.25 mg/ml), was added and after 6 min. the reaction was stopped by an addition of 100 µl 1M Na$_2$CO$_3$ and the supernatant was analyzed in an EAR340AT ELISA plate reader (SLT-Labinstruments, Austria) by measuring the absorbence at 405 nm. The strands were separated by melting by incubation with 20 µl 0.1M NaOH for 5 min. generating single stranded immobilized DNA template, which was once again washed with 50 µl binding solution, 50 µl 1×TE. The primer annealing was performed in 8 mM MgCl$_2$ and 20 mM Tris-HCl (pH 7.5) with the use of 1 pmol RIT332 (FIG. 2) in a volume of 13 µl by heating to 65° C. for 5 min. and then placed in room temperature for 10 min.

Mini Sequencing reactions

Figure 1:
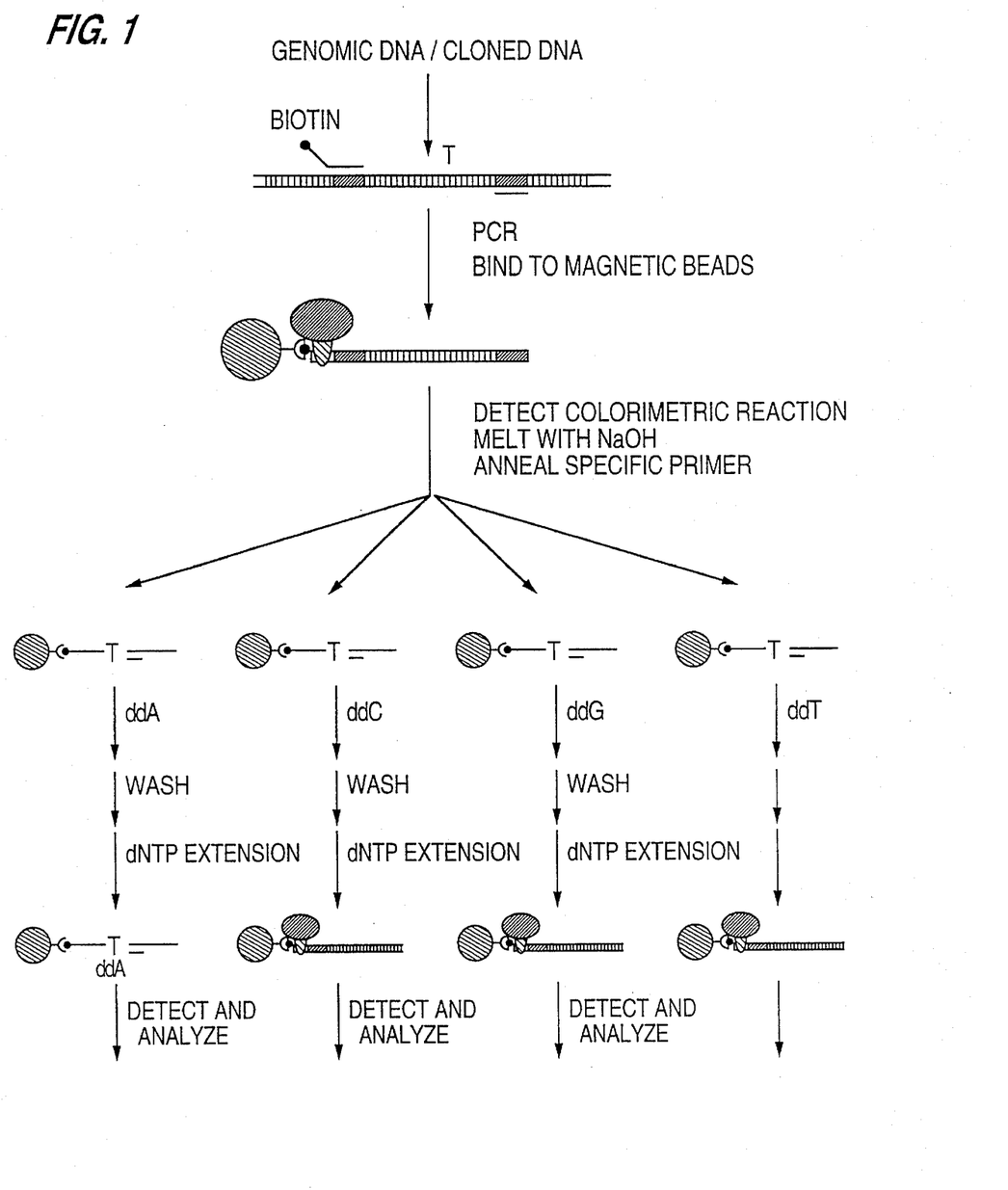
FIG. 1 shows a protocol for identifying a base in a single target position using the method according to the invention.

Six separate extension reactions with respect to the appropriate dideoxynucleotide were set up (one with only ddATP, one with only ddCTP, one with only ddGTP, one with only ddTTP, one with all four ddNTPS present and one without any of ddNTPs) in a total of 10 µl containing 2 µl of the annealing mixture, 17 mM Tris-HCl (pH7.5), 6 mM MgCl$_2$, 1 mM DTT, 1 µM of the appropriate dideoxynucleotide and 0.13 units of Sequenase® ver. 2. A schematic outline of the experiment is shown in FIG. 1. The dideoxy incorporation was performed at room temperature for 5 mins. and stopped by adding 20 µl 0.5M EDTA. Thereafter the beads were washed twice with 30 µl 10 mM Tris-HCl (pH 7.5). In the following extension step 200 µM dNTP concentration was used together with 25 mM Tris-HCl (pH 7.5), 12.5 mM MgCl$_2$, 1 mM DDT and 0.13 units Sequenase® in a total of 10 µl. In the aliquots where a dideoxynucleotide had not been incorporated, the Sequenase® leads to a chain extension and to full double stranded DNA being attached to the beads. After a 5 min. incubation in room temperature 20 µl 0.5M EDTA was added and the beads were washed with 40 µl DIANA buffer (Dynal AS, Norway) (0.1M Tris-HCl (pH 7.5), 0.15M NaCl, 0.1% Tween 20, 1 mM MgCl$_2$ and 10 mM β-mercaptoethanol).

Detection by DIANA

Figure 4:
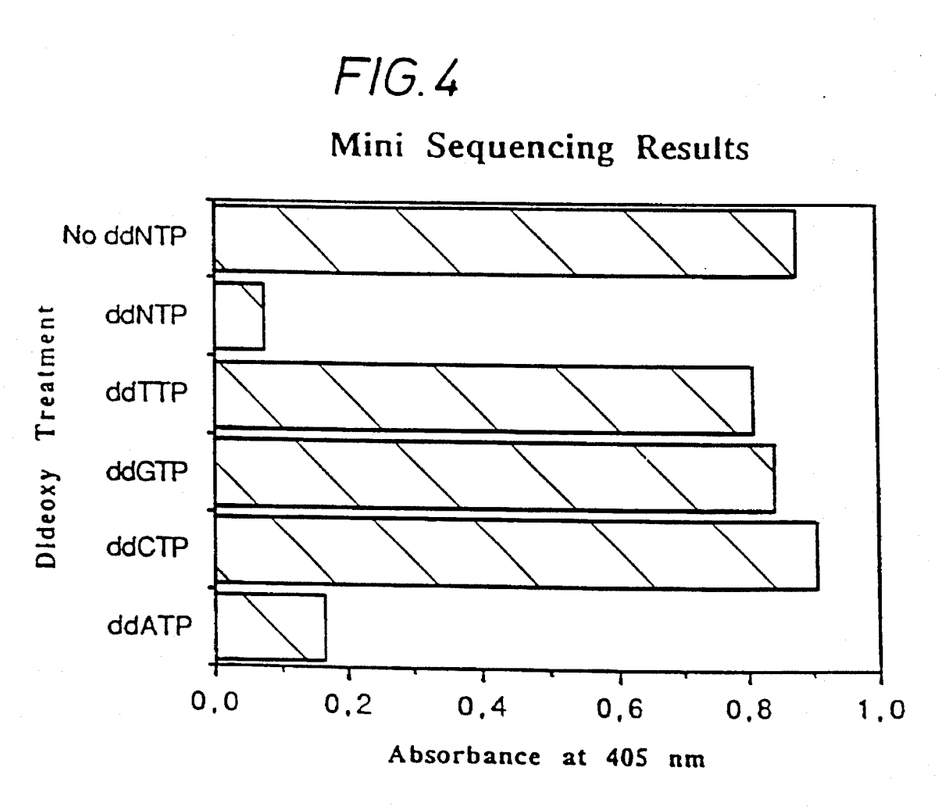
FIG. 4 is a graph showing the results obtained in the Example of the method according to the invention.

The results were detected by DIANA (Wahlberg, J., Lundeberg, J., Hultman, T. and Uhlén, M. (1990) "General colorimetric method for DNA diagnostics allowing direct solid-phase genomic sequencing of the positive samples." Proc. Natl. Acad. Sci U.S.A. 87, 6569–6573). The beads with the immobilized DNA were mixed with 50 µl of the fusion protein, lacI-β-galactosidase (Dynal AS, Norway), and incubated for 20 minutes. Excess of the fusion protein was removed by washing the beads 4 times with DIANA buffer (Dynal AS, Norway) and changing to new tubes in the last step in order to avoid background due to coating of the walls. 100 µl of chromogenic substrate, ortho-nitrophenyl-β-D-galactoside (ONPG, 1.25 mg/ml), was added and after 6 min. the reaction was stopped by an addition of 100 µl 1M Na$_2$CO$_3$ and the supernatant was analyzed in an EAR340AT ELISA plate reader (SLT-Labinstruments, Austria) by measuring the absorbence at 405 nm. The results are shown in FIG. 4. The assay show that a low signal is obtained when all four dideoxynucleotides (ddNTP) are used as well as when only ddATP is used. Since the complementary base next to the 3'-end of the sequencing primer is a dideoxythymidine, the result demonstrates that the assay can be used to detect a base sequence at a specific point.

EXAMPLE 2

Template preparation

A HIV reverse transcriptase gene fragment from a patient showing AZT resistance was PCR-cloned (Petterson, B, et al unpublished data) into the vector pRIT 28 by using the primers RIT 331 and RIT 333. E.coli RR1ΔM15 was transformed and blue/white selectivity was used (Langley E. K., et al (1975) loc. cit.) PCR amplification was carried out by lysing a bacterial colony in 10 µl 20 mM Tris-Cl (pH 8.7) at 99° C. for 5 minutes. Then 1 µl of the lysate was added to 5 pmol Primer set A, 200 µM dNTP, 20 mM Tris-Cl, pH 8.7, 2 mM MgCl$_2$, 0.1% Tween® 20™ and 0.5 units AmpliTaq DNA polymerase (Cetus, Calif., USA) making up a total volume of 50 µl. The temperature profile included a 0.5 min. denaturation step at 95° C. and a 1.5 min. annealing/extension step at 70° C., these steps were repeated 30 times. A GeneAmp PCR System 9600 (Perkin Elmer, Calif., USA) was used for both lysing the bacterial colony and running the reactions. The PCR product was immobilized on paramagnetic beads (Lea, T., et al (1988) loc. cit.) with covalently coupled streptavidin, Dynabeads® M280. The beads were used as described by the manufacturer (Dynal AS, Norway). Single stranded DNA was obtained by removing the supernatant after incubation of the immobilized PCR product in 0.10M NaOH for 10 minutes. The immobilized single stranded DNA was washed with 50 µl 10 mM Tris-Cl (pH 7.5), 1 mM EDTA, 2M NaCl followed by 50 µl 10 mM Tris-Cl (ph 7.5). After washing, 20 mM Tris-Cl (pH 7.5), 8 mM MgCl$_2$ and 1 pmol sequencing primer were added to a final volume of 13 µl. The mixture was incubated at 65° C. for 5 minutes and then cooled to room temperature.

Mini-sequencing

The dideoxynucleotide incorporation reactions were performed in a mixture of 1 µl (⅓ of a 50 µl PCR amplification reaction) of the template/primer-fragment immobilized on paramagnetic beads, 0.13 units Sequenase® version 2.0 (United States Biochemical, USA), 0.5 µl 10 µM of a single ddNTP, and a buffer containing 25 mM Tris-Cl (pH 7.5), 12.5 mM MgCl$_2$ and 2.5 mM DTT in a final volume of 10 µl. After incubation at room temperature for 5 minutes, the beads were washed with 50 µl 10 mM Tris-Cl (pH 7.5), 1 mM EDTA, 2M NaCl, 1% Tween 20™ followed by 50 µl 10 mM Tris-Cl (pH 7.5), 1 mM EDTA, 2M NaCl and finally with 50 µl 10 mM Tris-Cl (pH 7.5). The volume was adjusted to 5 µl with 10 mM Tris-Cl (pH 7.5). Control fragments were incubated with DNA polymerase in the absence of ddNTPS and zero control fragments in the presence of all ddNTPS. The different samples were subsequently analyzed with the ELIDA.

ELIDA

Samples from the above described mini-sequencing pre-incubation were assayed for full primer extension by the ELIDA. The assay was performed using an LKB 1250 luminometer and a potentiometric recorder. The luminometer was calibrated to give a response of 10 mV for the internal light standard. The luminescence output was calibrated by the addition of a known amount of ATP or ppi. The reaction was carried out at room temperature. The standard assay volume was 0.2 ml and contained the following components: 0.1M Tris-acetate (pH 7.75), 2 mM EDTA, 10 mM magnesium acetate, 0.1% BSA, 1 mM DTT, 0.4 mg/ml polyvinylpyrrolidone 360,000, 2 µM dNTP, 100 µg/ml D-luciferin (BioOrbit, Finland), 4 µg/ml L-luciferin (BioOrbit, Finland), 0.3 units/ml ATP-sulfurylase (Sigma, USA) and purified luciferase (Enzymatix, UK). The amount of luciferase used gave a response of 1 V for 100 pmol ATP in a volume of 1 ml. After five minutes of preincubation, adenosine 5'-phosphosulfate, NaF and dNMP were added to final concentrations of 2 µM, 5 mM and 0.4 mM, respectively. The reaction was started after the addition of 5 µl of template/primer-fragments, taken from the dideoxy incorporation, by the addition of 0.13 units of Sequenase®. The reaction was completed within 5 minutes.

RESULTS

Principle of the mini-sequencing method

The principle of the mini-sequencing method is outlined in FIG. 1 in which the presence or absence of a T residue is investigated. The specific DNA-fragment of interest is amplified by PCR with one of the primers biotinylated in the 5' end. The PCR-amplified DNA is immobilized on magnetic beads containing covalently coupled streptavidin and subsequently converted into single stranded form by washing with NaOH, and a primer is annealed to the single stranded DNA. The template/primer-fragments are then divided into four different aliquots which are separately treated with one of the four ddNTPs in the presence of the polymerase. After the reaction, the resulting fragments are washed and used as substrate in a primer extension reaction with all four dNTPs present (see FIG. 1). The progress of the DNA-directed polymerisation reactions are monitored with the ELIDA. Incorporation of a dideoxynucleotide in the first reaction will prevent the formation of pyrophosphate during the subsequent "chase" reaction. In contrast, no dideoxynucleotide incorporation gives extensive pyrophosphate release during the "chase" reaction and this will lead to generation of light through the ELIDA reactions. From the ELIDA results, the first base after the primer is easily deduced. It is also possible to include both a negative control, which is incubated with all ddNTPs, and a positive control, which is incubated with DNA polymerase in the absence of dNTPs.

Mini-sequencing of a specific DNA-fragment

Incorporation of a single ddNTP was observed only when the complementary dideoxynucleotide (ddATP) was present during the polymerase reaction. No incorporation of non-complementary bases was observed under the conditions used. The formation of ppi was detected by the ELIDA during the "chase" reaction only when template/primer-fragments were incubated with noncomplementary bases. When a complementary base was incorporated, no extension of the DNA was possible due to the lack of a free 3' OH group. The same result as above was obtained if the DNA-fragments (in the first step) were incubated with four different mixtures of three ddNTPs (not shown). It is important to note that a DNA polymerase lacking exonuclease activity must be used to obtain clean signals, although it is known that exonuclease activity of certain polymerases can be suppressed, e.g. by fluoride ions. It is also important to use low concentrations of nucleotides (0.05–5 µM) to avoid incorporation of non-complementary bases (data not shown).

Sensitivity

In the experiments presented above 1/13th of a 50 µl PCR amplification reaction was used per ELIDA test. However, both lower and higher amounts can be used. The initial rate and the extent of ppi formation during primer extension of a 161 bases long DNA-fragment as a function of DNA concentration was determined. Both the initial rate and the extent of ppi formed in the ELIDA are proportional to the DNA concentration in the interval tested (1/130 to 2/13 of a 50 µl PCR amplification reaction). The amount of DNA could be further increased as well as the binding capacity of the solid support to increase the signal of the assay. The upper limit for the present assay (in a total volume of 200 µl) is 200 pmol ppi formed. The lower limit is mainly determined by the length of the DNA-fragment used, (as the signal is proportional to the amount of nucleotides incorporated during the primer extension reaction), the volume used and by contamination of ppi in the different solutions. Both these latter factors can be modified if necessary.

We claim:

1. A method of identifying the base in a target position in a DNA sequence of sample DNA, wherein:

(A) said sample DNA is subjected to amplification, thereby forming amplified, double-stranded DNA;

(B) said amplified, double-stranded DNA is immobilised on a solid support at one end of one strand of said double-stranded DNA, thereby forming an immobilised strand and a non-immobilised strand, and then subjected to strand separation, whereby said non-immobilised strand is removed and immobilised single-stranded DNA remains;

(C) an extension primer is provided, which hybridises to said immobilised single-stranded DNA at a position immediately adjacent to said target position;

(D) each of four aliquots of said immobilised single-stranded DNA is subjected to a polymerase reaction in the presence of a dideoxynucleotide, each aliquot using a different dideoxynucleotide, whereby only in the aliguot using the dideoxynucleotide complementary to the base at said target position will said dideoxynucleotide become incorporated into said immobilised single-stranded DNA to form dideoxy-blocked DNA;

(E) each of said four aliquots are subjected to extension in the presence of all four deoxynucleotides, whereby the DNA which did not form dideoxy-blocked DNA is extended to form double-stranded DNA, while the dideoxy-blocked DNA remains as non-extended DNA; and (F) the formation of double-stranded DNA and/or non-extended DNA is identified to indicate which dideoxynucleotide was incorporated into said immobilised single-stranded DNA, and hence which base was present at said target position.

2. The method of claim 1, wherein, in step (A), said sample DNA is amplified by an in vitro amplification reaction using a first primer which is immobilised on a solid support or which is provided with means for immobilisation on a solid support.

3. The method of claim 2, wherein said first primer includes a non-hybridising region which upon chain extension creates, in double-stranded form, a recognition site for a DNA-binding protein carrying a label, and wherein, in step (F), the formation of double stranded DNA by chain extension is identified by adding the labeled DNA-binding protein to said aliquots and determining the binding of said labeled DNA-binding protein to the DNA in each of said aliquots.

4. The method of claim 2, wherein said first primer carries biotin as means for immobilisation.

5. The method of claim 2, wherein:

in step (A), said in vitro amplification reaction further uses a second primer for introducing a loop structure into the amplified DNA, wherein said second primer hybridises to a region A at the 3' terminus of said sample DNA and/or to a region B extending 3' from said region A, said second primer having a 3' terminal sequence which hybridises to at least a portion of regions A and/or B of said sample sequence while having at its 5'-end a sequence substantially identical to A, whereby said amplification reaction of step (A) produces double-stranded sample DNA having at the 3'-end of the sample sequence, in the following order, the region A, a region capable of forming a loop, and a sequence A' complementary to sequence A; in step (B), said amplified, double-stranded DNA, if not already immobilised, is immobilised on a solid support at one end of one strand of said double-stranded DNA, thereby forming an immobilised strand an a non-immobilized strand, and is subjected to strand separation, whereby said non-immobilised strand is liberated and immobilised single-stranded DNA remains; and in step (C), said extension primer is provided by permitting or causing said region A' of said immobilised strand to hybridise to region A of said immobilised strand at a temperature above the self-annealing temperature of said second primer, thereby forming said loop, whereby the hybridised portion of said loop forms said extension primer.

6. The method of claim 1, wherein, in step (F), the formation of double stranded DNA is identified by detecting pyrophosphate liberated in the extension reaction.

7. The method of claim 6, wherein said pyrophosphate is detected by reacting said aliquots with luciferase in the presence of luciferin, wherein emission of light is an indicator or measure of pyrophosphate.

\* \* \* \* \*